(12) United States Patent
Mohe et al.

(10) Patent No.: US 8,586,710 B2
(45) Date of Patent: Nov. 19, 2013

(54) PROCESS FOR GRAM SCALE PRODUCTION OF PEG-R-METHUG-CSF

(75) Inventors: Nikhil Umesh Mohe, Mumbai (IN); Dinesh Kumar Paliwal, Mumbai (IN); Divya Lal Saksena, Mumbai (IN); Chandrakesan Muralidharan, Mumbai (IN); Rakesh Shekhawat, Mumbai (IN); Sagar Satyanarayan Zawar, Mumbai (IN)

(73) Assignee: USV, Ltd., Mumbai (IN)

( * ) Notice: Subject to any disclaimer, the term of this patent is extended or adjusted under 35 U.S.C. 154(b) by 92 days.

(21) Appl. No.: 13/123,558

(22) PCT Filed: May 4, 2009

(86) PCT No.: PCT/IN2009/000262
§ 371 (c)(1),
(2), (4) Date: Apr. 11, 2011

(87) PCT Pub. No.: WO2010/089756
PCT Pub. Date: Aug. 12, 2010

(65) Prior Publication Data
US 2011/0196134 A1    Aug. 11, 2011

(30) Foreign Application Priority Data

Oct. 20, 2008   (IN) .......................... 2261/MUM/2008

(51) Int. Cl.
*C07K 1/02*       (2006.01)
*C07K 1/107*      (2006.01)
*C07K 14/535*     (2006.01)
*A61K 38/19*      (2006.01)

(52) U.S. Cl.
USPC ............. 530/351; 530/350; 530/402; 514/3.2

(58) Field of Classification Search
None
See application file for complete search history.

(56) References Cited

U.S. PATENT DOCUMENTS

| | | | |
|---|---|---|---|
| 5,824,778 A * | 10/1998 | Ishikawa et al. ............. | 530/351 |
| 5,824,784 A | 10/1998 | Kinstler et al. | |
| 7,884,075 B2 * | 2/2011 | Scheiflinger et al. ........ | 514/14.1 |
| 2004/0176569 A1 | 9/2004 | Piquet et al. | |
| 2009/0252703 A1 | 10/2009 | Gegg, Jr. et al. | |
| 2010/0016217 A1 | 1/2010 | Jain et al. | |
| 2010/0035814 A1 | 2/2010 | Peschke et al. | |

OTHER PUBLICATIONS

Holtschlag et al., BioProcess International, 6 (7), 52, 2008.*
Kinstler, O.B., et al., "Characterization and Stability of N-terminally PEGylated rhG-CSF," Pharmaceutical Research, (1996) vol. 13, No. 7, p. 996-1002.
Pavisic, R., et al., "Recombinant Human Granulocyte Colony Stimulating Factor Pre-Screening and Screening of Stabilizing Carbohydrates and Polyols," International Journal of Pharmaceutics (2010) 387, p. 110-119.
Piedmonte, D.M. & Treuheit, M.J., "Formulation of Neulasta (pegfilgrastim)," Advance Drug Delivery Reviews (2008), 60, 50-58.
Carpenter, J.F., et al., "Inhibition of Stress-Induced Aggregation of Protein Therapeutics," Methods of Enzymololgy, (1999) vol. 309, p. 236-255.
Krishnan, S., et al., "Aggregation of Granulocyte Colony Stimulating Factor Under Physiological Conditions: Characterization and Thermodynamic Inhibition," Biochemistry (2002) 41, p. 6422-6431.
Kinstler, O.G., et al., "Mono-N-terminal Poly(ethylene glycol)-protein conjugates," Advanced Drug Delivery Reviews, (2002) 54, p. 477-485.
Rajan, R.S., et al., "Modulation of Protein Aggregation by Polyethylene Glycol Conjugation: GCSF as a case study," Protein Science (2006) 15, p. 1063-1075.
Yun, Q., et al., "Reproducible Preparation and Effective Separation of PEGylated Recombinant Human Granulocyte Colony-stimulating Factor with Novel "PEG-pellet" PEGylation Mode and Ion-exchange Chromatography," Journal of Biotechnology (2005) 118, p. 67-74.

* cited by examiner

*Primary Examiner* — Elly-Gerald Stoica
(74) *Attorney, Agent, or Firm* — Pharmaceutical Patent Attorneys, LLC

(57) ABSTRACT

The present invention relates to a process for improving pegylation reaction yield of r-metHuG-CSF comprising conjugating r-metHuG-CSF to a PEG aldehyde at a free amine moiety at the N terminal end on the G-CSF in presence of a reducing agent in a pegylation buffer solution comprising a polyol having the formula $C_nH_{2n+2}O_n$ where n is from 3 to 6, or a carbohydrate, or a derivative thereof wherein the concentration of said polyol or carbohydrate or derivative thereof is in the range of 0.1% to 10% w/w.

4 Claims, 12 Drawing Sheets

Figure 1:
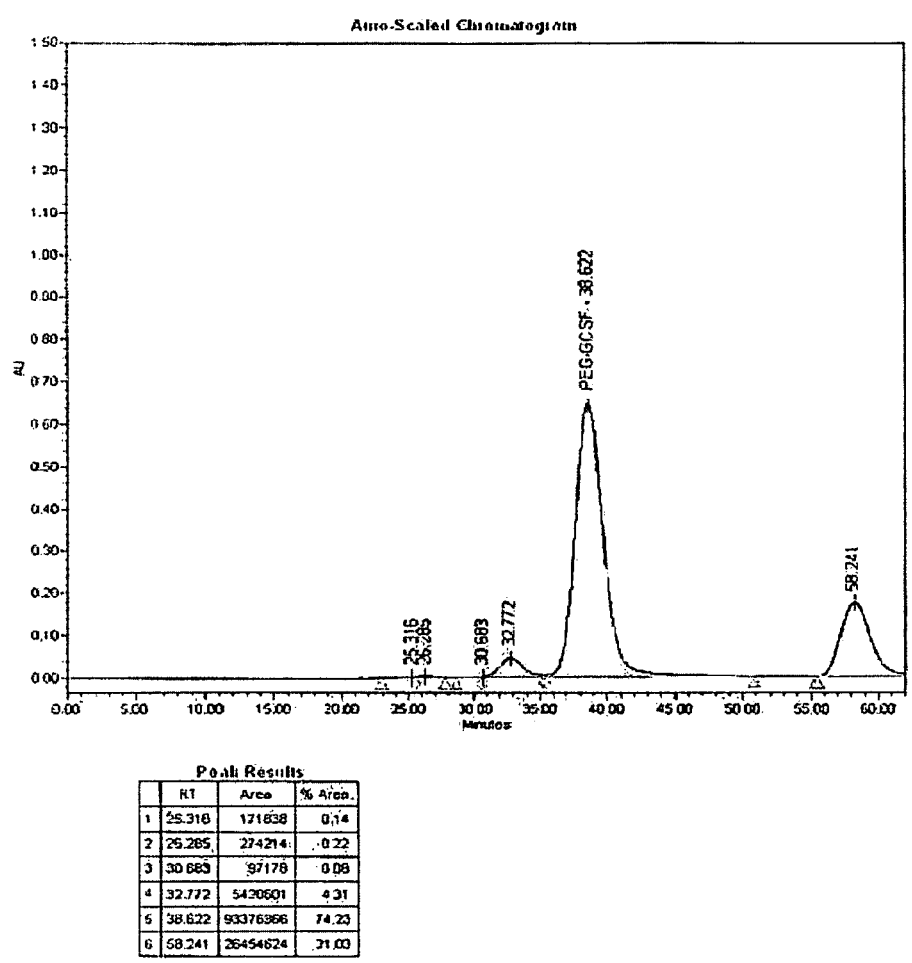

| | Peak Name | RT | Area | % Area |
|---|---|---|---|---|
| 1 | | 25.191 | 379130 | 0.12 |
| 2 | | 29.367 | 383133 | 0.12 |
| 3 | | 31.579 | 21558067 | 6.68 |
| 4 | PEG GCSF | 37.609 | 270843289 | 83.91 |
| 5 | | 57.886 | 29615506 | 9.18 |

PROCESS FOR GRAM SCALE PRODUCTION OF PEG-R-METHUG-CSF

RELATED APPLICATIONS

This application claims priority from PCT Application No. PCT/IN2009/000262 filed on May 4, 2009, which in turn claims priority from Indian Provisional Application No. 2261/MUM/2008 filed on Oct. 10, 2008.

TECHNICAL FIELD OF THE INVENTION

The present invention relates to the field of protein modification, and, more specifically, to an improved process for the attachment of water soluble polymer selectively to N terminal of proteins or analogs thereof. More specifically the present invention relates to an improved process of PEGylation of r-metHuG-CSF, characterized in that the reaction is carried out in the presence of sugar alcohol, as for example sorbitol.

BACKGROUND OF INVENTION

Proteins for therapeutic use are currently available in suitable forms in adequate quantities largely as a result of the advances in recombinant DNA technologies. The availability of recombinant proteins has endangered advances in protein formulation and chemical modification. One goal of such modification is protein protection. Chemical attachment may effectively block a proteolytic enzyme from physical contact with the protein backbone itself, and thus prevent degradation. Additional advantages include, under certain circumstances, increasing the stability and circulation time of the therapeutic protein and decreasing immunogenicity. One such method commonly used for protein modification is by covalent attachment of water soluble polymers.

Polyethylene glycol ("PEG") is one such chemical moiety which has been used in the PEGylation of therapeutic protein products. The US FDA has approved PEG for use as a vehicle or base in foods, cosmetics and pharmaceuticals, including injectable, topical, rectal and nasal formulations. Molecules coupled to PEG become non-toxic, nonimmunogenic, soluble in water and many organic solvents, and surfaces modified by PEG attachment become hydrophillic and protein rejecting.

The FDA has approved several PEGylated polypeptides as therapeutics and more are undergoing clinical investigation. In 1990, pegademase (Adagen) received approval for the treatment of severe combined immunodeficiency (SCID). Pegaspargase (Oncaspar) approved in 1994, contains the pegylated enzyme L-asparaginase, used clinically in combination with chemotherapy for the treatment of acute lymphocytic leukaemia, acute lymphpblastic leukaemia and chronic myelogenous leukaemia. In 2001, peginterferon α2b (PegIntron) became available as a once-a-week treatment for hepatitis C. Peginterferon α2a (Pegasys) approved in 2002 used a second generation, branched PEG of 40 kDa conjugated through a ε-$NH_2$ group of lysine used as spacer to interferon α2a increased the half life of IFN-α2a from 9 to 77 hours. A pegylated form of human growth hormone antagonist called pegvisomant (Somavert) was approved by FDA in 2003 for the treatment of acromegaly. Doxil, a pegylated liposomal formulation of doxorubicin was approved in 1995 for the treatment of Kaposi's sarcoma. Pegfilgrastim (Neulasta), approved in 2002, is a pegylated form of the earlier drug filgrastim (Neupogen) used for the treatment of neutropenia. PEGylation has taken 20 years to emerge as a viable pharmaceutical tool. Over the period there have been important advances in the chemistry of PEGylation, in the generation of biomolecule therapeutics and in understanding PEG-biomolecule conjugates. PEGylation is now established as the method of choice for improving the pharmacokinetics and pharmacodynamics of protein pharmaceuticals.

A variety of active PEGs have been prepared. mPEG succinimidyl succinate and mPEG succinimidyl carbonate were the reagents used and approved by US FDA. The reagents had the limitation of forming weak linkages between the PEG moiety and protein, potential unwanted side reactions, contamination, and restriction to low MW PEGs. The above limitations were overcome by use of mPEG-propionaldehyde which was easier to prepare. PEG aldehydes are inert toward water and react primarily with amines. Inertness toward water is desired, not only because of efficiency of storage, preparation, and application, but also because it permits stepwise linkage, in aqueous media, of molecules to surfaces and molecules to molecule. mPEG aldehyde has essentially all the properties of ideal PEG derivative i.e. reactive with nucleophillic groups (typically amino) on proteins and surfaces; stable in aqueous media and on the shelf; easily prepared and characterized; and capable of coupling to proteins without reducing protein activity.

U.S. Pat. No. 5,824,784 assigned to Amgen claims a substantially homogenous preparation of N-terminally monoPEGylated G-CSF or analog thereof and a method for attaching a polyethylene glycol to a G-CSF molecule wherein the PEG moeity has single aldehyde group. The PEGylation process claims reacting G-CSF with polyethylene glycol under reducing alkylation conditions at a pH sufficiently acidic to selectively activate the alpha amino group at the amino terminus of G-CSF. The process discloses the addition of a 5-fold molar excess of methoxypolyethylene glycol aldehyde of average MW, 6 kDa to a cooled (4° C.) stirred solution of rhG-CSF (1 ml, 5 mg/ml) in 100 mM sodium phosphate, pH 5, containing 20 mM $NaCNBH_3$. The stirring of the reaction mixture was continued at the same temperature The mono-mPEG-GCSF derivative was purified by ion exchange chromatography using HiLoad 16/10 S SEPHAROSE HP column and eluted with a linear 400 minute gradient from 0% to 45% 20 mM sodium acetate, pH 4, containing 1M NaCl. The % composition of N terminally mono-mPEG-GCSF obtained by reductive alkylation is not disclosed. A comparative stability analysis of N-terminally momopegylated G-CSF obtained by amide linkage (derived by using N-hydroxy succinimidyl ester of carboxymethyl methoxy polyethylene glycol as nucleophile) and the other obtained by amine linkage for 8 weeks yielded 82% purity with respect to one having amine linkage between the protein and the mPEG-aldehyde. A surprising result was observed as the amine linkage produced a material with far fewer aggregates against the one with amide linkage.

The present invention discloses a simple and improved process to enhance the efficiency of pegylation process by addition of a polyol having the formula $C_nH_{2n+2}O_n$ where n is from 3 to 6, or a carbohydrate, or a derivative thereof. Pursuant to following the Example 2 of U.S. Pat. No. 5,824,784, it was surprisingly found that addition of a polyol having the formula $C_nH_{2n+2}O_n$ where n is from 3 to 6, or a carbohydrate, or a derivative thereof to the pegylation buffer after buffer exchange from the storage buffer to the pegylation buffer and maintenance of the concentration of said polyol having the formula $C_nH_{2+2}O_n$ where n is from 3 to 6, or a carbohydrate, or a derivative thereof during the entire pegylation process not only increases the pegylation yield but also results in the formation of pure monopegylated r-metHuG-CSF with >80% purity thus minimising the formation of aggregates. Moreover the addition of polyol having the formula $C_nH_{2n+2}O_n$ where n is from 3 to 6, or a carbohydrate, or a derivative thereof leads to the minimal amount of unreacted r-metHuG-CSF as compared to the process carried out in the absence of the same. Kinstler et al., has investigated the liquid stability of rhG-CSF after PEG with an average molecular weight of 6000 daltons covalently attached to the N-terminal methionine wherein the covalent attachment was effected either through alkylation and acylation. The N-terminally PEGylated rhG-CSF conjugates were purified by cation exchange chromatography. Physical characterization indicated no apparent differences in the rhG-CSF molecules that were conjugated with either method. Stability, in liquid at elevated temperatures, of these conjugated molecules indicated that the primary pathway of degradation was aggregation. Conjugation through alkylation offered the distinct advantage of decreasing, by approximately 5 times, the amount of aggregation present as compared to acylation. Therefore, it was suggested that the increased aggregation observed with the acylation conjugation method may result from the charge neutralization of the N-terminal a-amino group of rhG-CSF. The detrimental effects of aggregation in parenteral formulations of therapeutic proteins affirms the importance of minimizing this type of degradation.

Protein aggregation and subsequent deposition as insoluble fibrils or amorphous precipitates is responsible for a number of diseases such as Alzheimer's disease, Parkinson's disease, Huntington's disease, and systemic amyloidosis. Protein aggregation is also a dominant degradation pathway for therapeutic proteins, potentially occurring during all phases of production, purification, shipping, storage, and administration. Protein aggregates in parenterally delivered protein formulations can cause adverse reactions in patients ranging from immune responses to anaphylactic shock. There is always a need to have stable parenteral formulations by minimizing the aggregates formation affecting the purity and activity of proteins over its shelf life.

Carpenter et al., investigated the aggregation of rhGCSF, a protein that rapidly aggregates and precipitates at pH 6.9 and 37° C. It was found that native monomeric rhGCSF reversibly forms a dimer under physiological conditions and that the dimeric species does not participate in the irreversible aggregation process. Sucrose, a thermodynamic stabilizer, inhibits the aggregation of rhGCSF. Carpenter et al. had postulated that sucrose acted by reducing the concentration of structurally expanded species, consistent with the hypothesis that preferential exclusion favors most compact species in the native state ensemble.

Rajan et al., in a study conducted under physiological pH and temperature, showed that N-terminal attachment of a 20 kDa PEG moiety to GCSF had the ability to 1) prevent protein precipitation by rendering the aggregates soluble, and 2) slowed the rate of aggregation relative to GCSF.

Yun et al., disclosed a novel mPEG derivative, containing a reaction group of 1-methyl pyridinium toluene-4-sulfonate conjugated to rhGCSF and consensus interferon to obtain homogeneous mono-PEGylated proteins which were identified by high performance size-exclusion and MALDI-TOF mass spectrometry.

Aggregation is agglomeration of proteins that frequently is irreversible when introduced into physiologic fluids, leading to inactivation or increased immunogenicity. Aggregation is a common problem with protein pharmaceuticals and may compromise process isolation yields, limit shelf life, cause failure in manufacturing, and prevent applications to new advances in delivery. Exposure of proteins to shear, agitation, and multiple surfaces is unavoidable and may induce aggregation.

Protein concentration is an important variable for ameliorating aggregation. The initial conformation related reaction leading to aggregation is expected to be first order but the subsequent aggregation of nonnative states is expected to be a second or higher order process because the frequency of collisions varies with concentration. Therefore, aggregation is expected to accelerate with increased protein concentration. Sorbitol (D-glucitol) is a polyol commonly used as an excipient in liquid parenteral biologic formulations and even as a food sweetening agent. Sorbitol provides effective protein stabilization in the liquid state and several marketed biologics are formulated in sorbitol including Neulasta and Neupogen.

Carbohydrates such as sucrose, glucose, mannose, and trehalose as well as polyhydric alcohols like glycerol, sorbitol, and mannitol have frequently also been used to enhance the solubility of proteins. This effect is presumably mediated through a combination of mechanisms including preferential hydration effects and increase in solvent surface tension as well as weak interactions with the surface of the proteins. The excellent biocompatibility of these compounds make them of general utility in this regard since little effect on protein structure and activity is usually seen in the presence of high concentrations of polyols, especially carbohydrates. The protein solubility problem is in many ways analogous to the protein folding problem in that very small differences between complex thermodynamic states account for the phenomena. It follows that an accurate description of the two critical states of interest, the structure of the surface hydration shell of the protein and the nature of the intermolecular contacts in the solid phase, is necessary to quantitatively account for the solubility of a particular macromolecule. Alteration of solubility using external variables suggest that only minor alterations of the solvent or solute should be sufficient to perturb protein solubility. Addition of physiologically acceptable compounds such as salts, sugars, and amino acids can be used to control protein solubility in an empirical manner. Since these same agents will sometimes enhance protein stability, the right combination of circumstances could result in a single compound providing stabilizing, solubilizing, and buffering capacity.

In addition to the above, use of polar organic solvents for enhancing the pegylation efficiency are already known in the prior art. PCT publication no. WO 02/28437 disclosed liquid-phase pegylation of growth hormone releasing factor, which allows to obtain regioselectively GRF-PEG conjugate having 1 PEG molecule covalently bound to the ε-amino group Lys12 characterized in that the reaction was carried out in a structuring solvent specifically alcohol and more specifically trifluoroethanol. The advantages cited were higher yields and the scaleability of the pegylation process.

Another PCT publication no. WO 2008/051383 A2 disclosed a method of producing a composition of matter wherein the method involved obtaining a pharmacologically active peptide, and conjugating the peptide to a pharmacologically acceptable PEG by reacting the peptide with a PEG-aldehyde compound at a free amine moiety on the peptide in a buffer solution comprising an alcohol co-solvent. The use of the method is particularly useful for pegylating peptides that are relatively insoluble in an aqueous medium, typically peptides with aqueous solubility below about 0.1 to 10 mg/ml. Additional benefits included acceleration of pegylation reaction and improved pegylation efficiency. The pegylation efficiency by reductive amination of peptide sequences benefits from the use of more hydrophobic alcohols and the efficiency enhancement afforded by fluoro alcohols was most advantageous to reductive amination reactions. The % of alcohols found to be beneficial was in the range of 30% to 70% v/v.

WO 2008/051383 A2 exemplified usage of Isopropyl alcohol(IPA), Trifluoroethanol (TFE), and hexafluoro-isopropyl alcohol (HFIPA) as co-solvents for enhancement in pegylation efficiency showing increased product yields for pegylating Calcitonin gene related peptides (CGRP) that were relatively insoluble in an aqueous medium, typically peptides with aqueous solubility below about 0.1 to 10 mg/ml. The mono-PEGylated peptide product was quantitated by integration of RP-HPLC chromatograms and reported as % product peak. 50% IPA and 50% TFE surprisingly showed 2.6 fold increase in product yield with IPA and 4.1 fold with TFE respectively. The PEGylation reaction yields in almost 42 CGRP peptides tested showed the reaction yields between about 50% to about 70% as against of less than 20% seen in the absence of the alcohol co-solvent. A variety of alcohol co-solvents were tested in the buffer solution for the conjugation reaction in an attempt to solubilize less soluble peptide and to improve conjugate yields.

The above prior art are applicable to the synthetic peptides produced by solid phase peptide synthesis or solution phase synthesis. However the harsh conditions when alcohols are used at such high concentration cannot be used for pegylating proteins. Moreover the PEGylation was carried out at concentration of 2 mg/ml in an amine free buffer (20 mM sodium phosphate, pH 6.0) whereas in case of proteins like rhG-CSF the pegylation has to be carried out at least at a concentration of 5 mg/ml and an acidic pH sufficient to drive the reaction to completion. Hence an essential element of the present invention is use of non-hazardous additives for increasing the pegylation efficiency specially of proteins. Also an inherent limitation of the prior art is the handling of volatile and hazardous alcohols limits the use for large scale operations. An essential element of the instant invention is surprising effect of increased pegylation efficiency and product yield by addition of a polyol or a carbohydrate or a derivative thereof to pegylation buffer in presence of a suitable reducing agent by keeping the r-metHuG-CSF in solubilized form. Another element of the instant invention is to develop a cost-effective and robust process for gram scale production of PEG-r-metHuG-CSF wherein the pegylation is carried out in the storage buffer of r-metHuG-CSF by just concentrating the protein by addition of polyol having the formula $C_nH_{2n+2}O_n$ where n is from 3 to 6, or a carbohydrate, or a derivative thereof, by adjusting the pH of the reaction medium to drive the pegylation reaction and conjugating the mPEG aldehyde to r-metHuG-CSF wherein the process is less time intensive and eliminates the initial step of buffer exchange. Still another element of the instant invention is reduction in use of stoichiometric molar ratio of r-metHuG-CSF to PEG from 1:5 to 1:2.5 wherein the cost reduction achieved is 1.5 fold over the process using 5 molar excess of PEG reagent. Another important element of the invention is eluting the monoPEGylated r-metHuG-CSF in the presence of polyol or carbohydrate or a derivative thereof using a salt gradient in the range of 0-500 mM and concentrating the pooled monoPEGylated r-metHuG-CSF against storage buffer consisting essentially of polyol or carbohydrate or a derivative thereof and a non ionic surfactant characterized in that the purity of concentrated monoPEGylated r-metHuG-CSF is ≥99%.

OBJECT OF THE INVENTION

There is always a need to have an improved and robust process for improving pegylation reaction yield for proteins. The principal object of the invention is a process for improving pegylation reaction yield of r-metHuG-CSF comprising conjugating r-metHuG-CSF to a PEG aldehyde at a free amine moiety at the N terminal end on the G-CSF in presence of a reducing agent in a pegylation buffer solution comprising a polyol having the formula $C_nH_{2n+2}O_n$ where n is from 3 to 6, or a carbohydrate, or a derivative thereof wherein the concentration of said polyol or carbohydrate or derivative thereof is in the range of 0.1% to 10% w/w. Another object of the invention is a process for gram scale production of PEG-r-metHuG-CSF comprising conjugating r-metHuG-CSF in storage buffer solution comprising a polyol having the formula $C_nH_{2n+2}O_n$ where n is from 3 to 6, or a carbohydrate, or a derivative thereof to a PEG aldehyde at a free amine moiety at the N terminal end on the r-metHuG-CSF in presence of a reducing agent the improvement being conjugating the r-metHuG-CSF in storage buffer solution having molarity in the range of 10 mM to 50 mM comprising a polyol having the formula $C_nH_{2n+2}O_n$ where n is from 3 to 6, or a carbohydrate, or a derivative thereof to a PEG aldehyde by elimination of step of buffer exchange to the pegylation buffer. Still another object of the invention is a process for gram scale production of PEG-r-metHuG-CSF comprising conjugating r-metHuG-CSF in storage buffer solution having molarity in the range of 10 mM to 50 mM comprising a polyol having the formula $C_nH_{2n+2}O_n$ where n is from 3 to 6, or a carbohydrate, or a derivative thereof to a PEG aldehyde at a free amine moiety at the N terminal end on the r-metHuG-CSF in presence of a reducing agent characterized in that the PEG aldehyde is added in stoichiometric molar ratio of 2.5 relative to r-metHuG-CSF. Still another object of the invention is a process for gram scale production of PEG-r-metHuG-CSF comprising conjugating r-metHuG-CSF in storage buffer solution comprising a polyol having the formula $C_nH_{2n+2}O_n$ where n is from 3 to 6, or a carbohydrate, or a derivative thereof to a PEG aldehyde at a free amine moiety at the N terminal, isolating the monoPEG-r-metHuG-CSF using ion exchange chromatography and eluting and concentrating the pooled monoPEGylated r-metHuG-CSF against storage buffer having molarity in the range of 10 mM to 50 mM consisting essentially of polyol having the formula $C_nH_{2n+2}O_n$ where n is from 3 to 6 or carbohydrate or a derivative thereof and a non ionic surfactant characterized in that the purity of concentrated monoPEGylated r-metHuG-CSF is ≥99%.

SUMMARY OF THE INVENTION

The present invention provides a process for selective pegylation of the proteins. More specifically, the present invention provides a process for improving pegylation reaction yield of r-metHuG-CSF comprising conjugating r-metHuG-CSF to a PEG aldehyde at a free amine moiety at the N terminal end on the G-CSF in presence of a reducing agent in a pegylation buffer solution comprising a polyol having the formula $C_nH_{2n+2}O_n$ where n is from 3 to 6, or a carbohydrate, or a derivative thereof wherein the concentration of said polyol or carbohydrate or derivative thereof is in the range of 0.1% to 10% w/w.

The present invention further provides a process for obtaining an enhanced pegylation reaction yield of r-metHuG-CSF wherein the reaction yield of the mono-PEGylated r-metHuG-CSF is at least 80%.

The present invention still further provides a process wherein the unreacted r-metHuG-CSF content in the pegylation reaction is less than 5%, preferably less than 2%.

The present invention further provides a process for producing monopegylated r-metHuG-CSF with ≥99% purity.

The present invention further provides a process for improving pegylation reaction yield of r-metHuG-CSF comprising conjugating r-metHuG-CSF to a PEG aldehyde at a free amine moiety at the N terminal end on the G-CSF in presence of a reducing agent in a pegylation buffer solution comprising a polyol having the formula $C_nH_{2n+2}O_n$ where n is from 3 to 6, or a carbohydrate, or a derivative thereof wherein the concentration of said polyol or carbohydrate or derivative thereof in the range of 0.1% to 10% w/w.

The present invention still further provides a is a process for gram scale production of PEG-r-metHuG-CSF comprising conjugating r-metHuG-CSF in storage buffer solution comprising a polyol having the formula $C_nH_{2n+2}O_n$ where n is from 3 to 6, or a carbohydrate, or a derivative thereof to a PEG aldehyde at a free amine moiety at the N terminal end on the r-metHuG-CSF in presence of a reducing agent the improvement being conjugating the r-metHuG-CSF in storage buffer solution having molarity in the range of 10 mM to 50 mM comprising a polyol having the formula $C_nH_{2n+2}O_n$ where n is from 3 to 6, or a carbohydrate, or a derivative thereof to a PEG aldehyde by elimination of step of buffer exchange to the pegylation buffer.

The present invention still further provides a a process for gram scale production of PEG-r-metHuG-CSF comprising conjugating r-metHuG-CSF in storage buffer solution having molarity in the range of 10 mM to 50 mM comprising a polyol having the formula $C_nH_{2n+2}O_n$ where n is from 3 to 6, or a carbohydrate, or a derivative thereof to a PEG aldehyde at a free amine moiety at the N terminal end on the r-metHuG-CSF in presence of a reducing agent characterized in that the PEG aldehyde is added in stoichiometric molar ratio of 2.5 relative to r-metHuG-CSF.

The present invention still further provides a process for gram scale production of PEG-r-metHuG-CSF comprising conjugating r-metHuG-CSF in storage buffer solution comprising a polyol having the formula $C_nH_{2n+2}O_n$ where n is from 3 to 6, or a carbohydrate, or a derivative thereof to a PEG aldehyde at a free amine moiety at the N terminal, isolating the monoPEG-r-metHuG-CSF using ion exchange chromatography and eluting and concentrating the pooled monoPEGylated r-metHuG-CSF against storage buffer having molarity in the range of 10 mM to 50 mM consisting essentially of polyol having the formula $C_nH_{2n+2}O_n$ where n is from 3 to 6 or carbohydrate or a derivative thereof and a non ionic surfactant characterized in that the purity of concentrated monoPEGylated r-metHuG-CSF is ≥99%.

BRIEF DESCRIPTION OF ACCOMPANYING DRAWINGS

The manner in which the objects and advantages of the invention may be obtained will appear more fully from the detailed description and accompanying drawings, which are as follows:

FIG. 1: SEC-HPLC profile of USV's crude pegylated r-metHuG-CSF wherein the pegylation is carried in absence of sorbitol.

Figure 2:
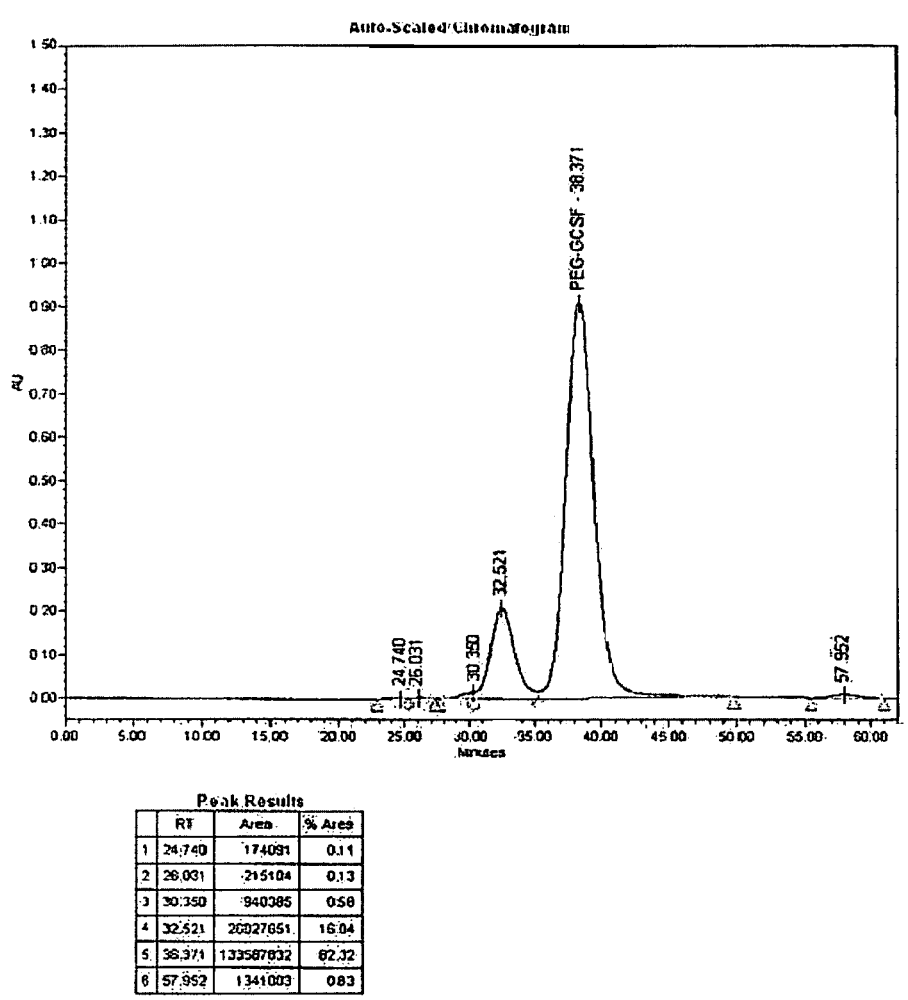

FIG. 2: SEC-HPLC profile of USV's crude pegylated r-metHuG-CSF wherein the pegylation is carried in presence of 5% sorbitol in pegylation buffer.

Figure 3:

FIG. 3: Non-reducing SDS-PAGE of USV's purified pegylated r-metHuG-CSF at different concentrations; Lane 1: USV's PEG-GCSF (2000 ng), Lane 2: USV's PEG-r-metHuG-CSF (1000 ng), Lane 3: USV's PEG-r-metHuG-CSF (200 ng), Lane 4: USV's PEG-r-metHuG-CSF (40 ng), Lane 5: USV's PEG-r-metHuG-CSF (20 ng), Lane 6: Neulasta (200 ng), Lane 7: Neulasta (40 ng), Lane 8: Protein MW ladder.

Figure 4:
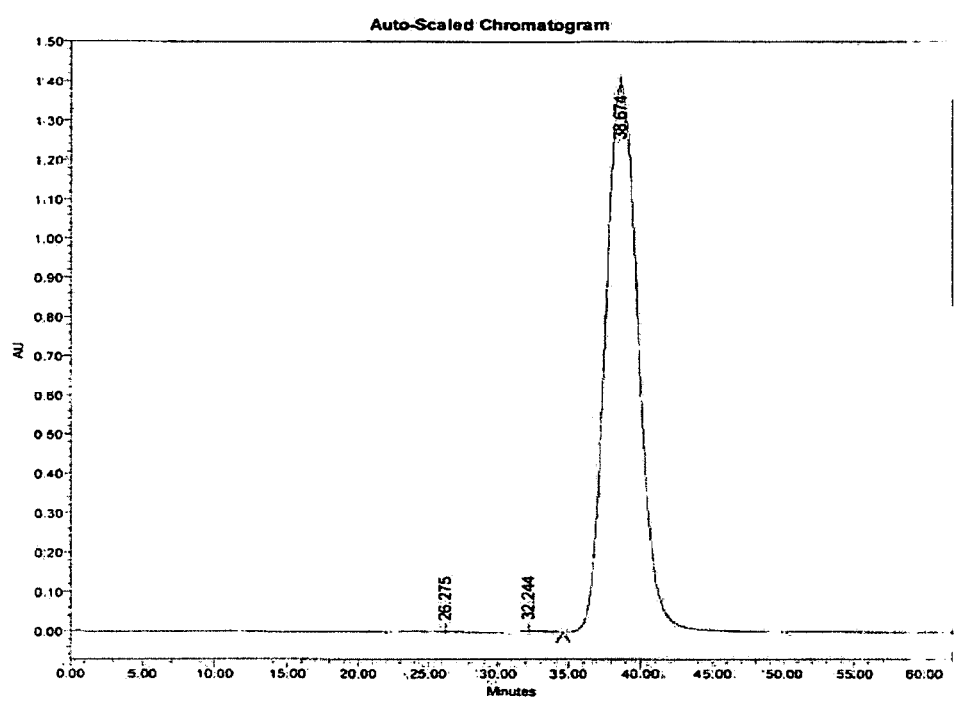

FIG. 4: SEC-HPLC profile of USV's monopegylated r-metHuG-CSF with a purity of >99%.

Figure 5:
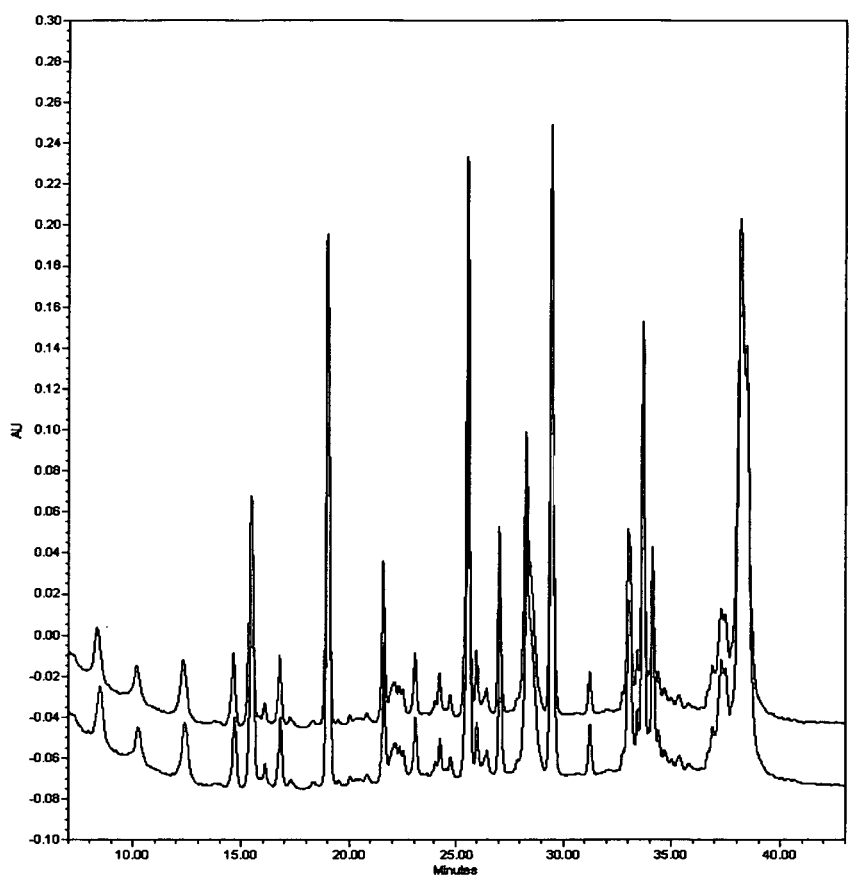

FIG. 5: HPLC endoproteinase SV8 peptide mapping profile of monopegylated r-metHuG-CSF; A: USV's monopegylatedr-metHuG-CSF, B:Neulasta.

Figure 6:
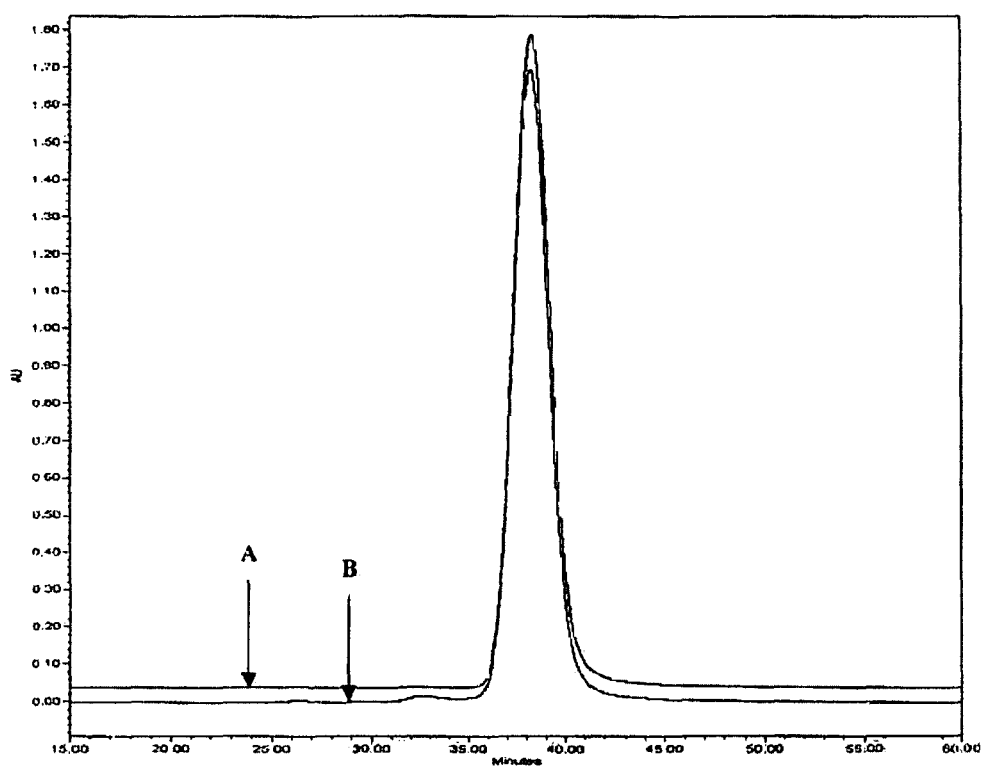

FIG. 6: SEC-HPLC profile of monopegylated r-metHuG-CSF with a purity of >99%; A: USV's monopegylated r-metHuG-CSF; B: Neulasta.

Figure 7:
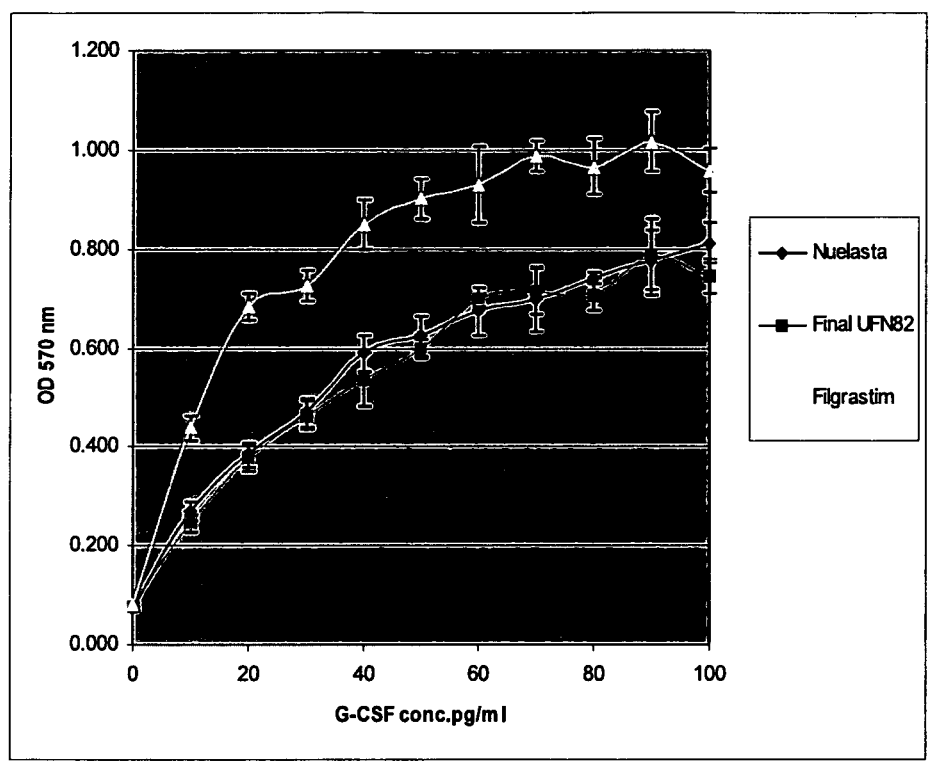

FIG. 7: Graph illustrating a comparison of in vitro bioactivity of USV's monopegylated r-metHuG-CSF compared against Neulasta & Neupogen.

Figure 8:
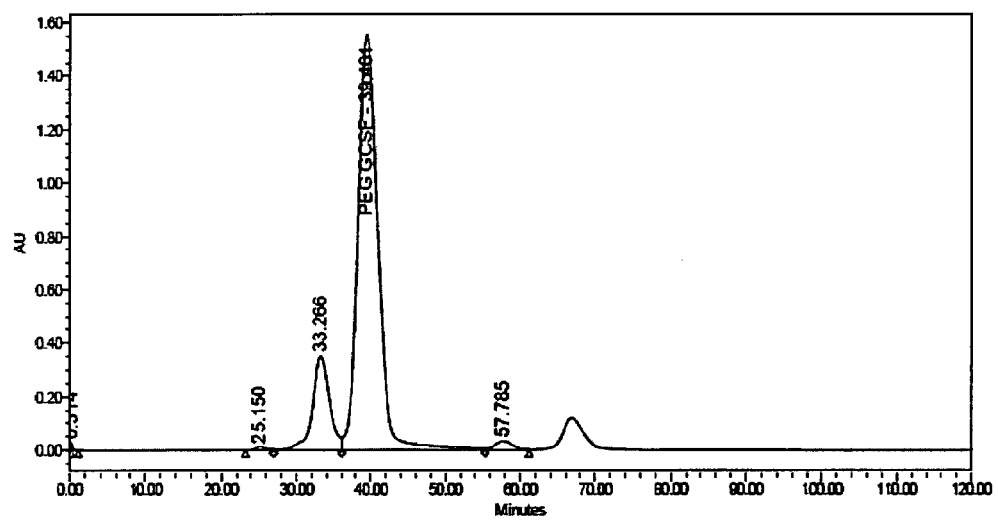

FIG. 8: SEC-HPLC profile of USV's crude pegylated r-metHuG-CSF wherein the pegylation is carried in presence of 5% sucrose in pegylation buffer.

Figure 9:
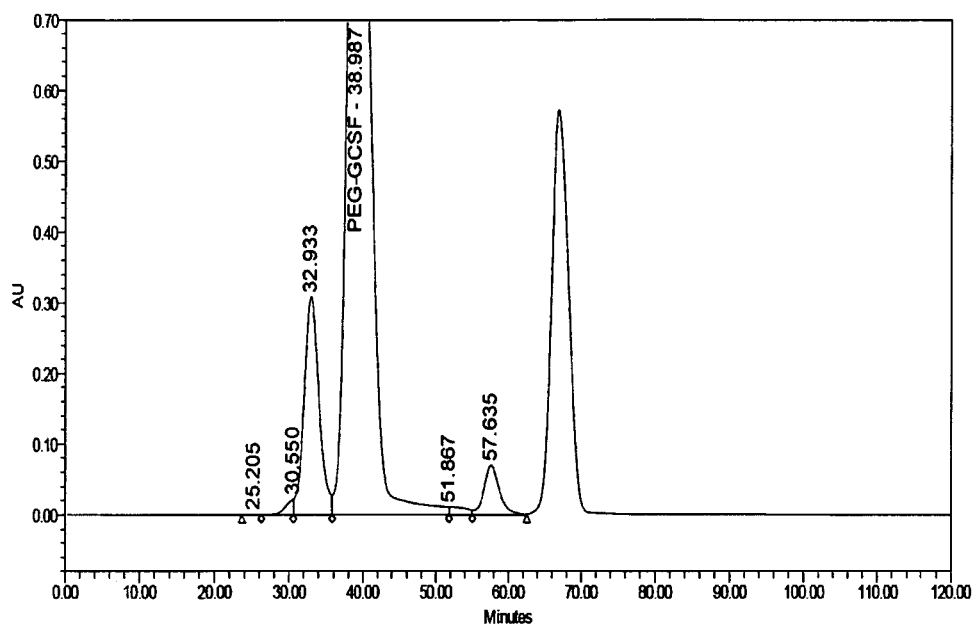

FIG. 9: SEC-HPLC profile of USV's crude pegylated r-metHuG-CSF of B.No. 0309/F (8 g scale) wherein the pegylation is carried in presence of 5% sorbitol in pegylation buffer FIG. 10: SEC-HPLC profile of USV's monopegylated r-metHuG-CSF with a purity of >99% of B.No. 0309/F (8 g scale).

Figure 11:
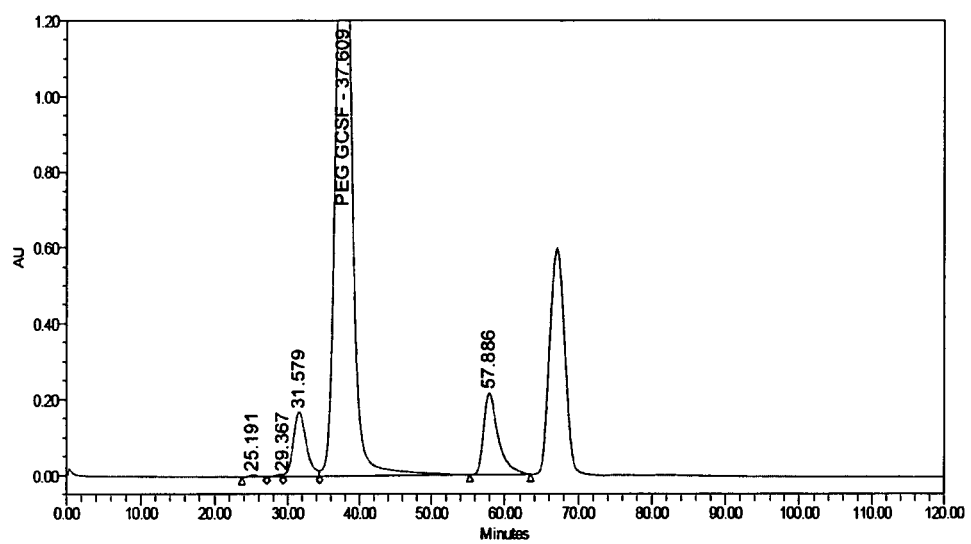

FIG. 11: SEC-HPLC profile of USV's crude pegylated r-metHuG-CSF wherein the pegylation is carried in presence of 5% sorbitol in acetate buffer, pH 5.0 with r-metHuG-CSF: mPEG propional dehyde ratio of 1:2.5.

Figure 12:
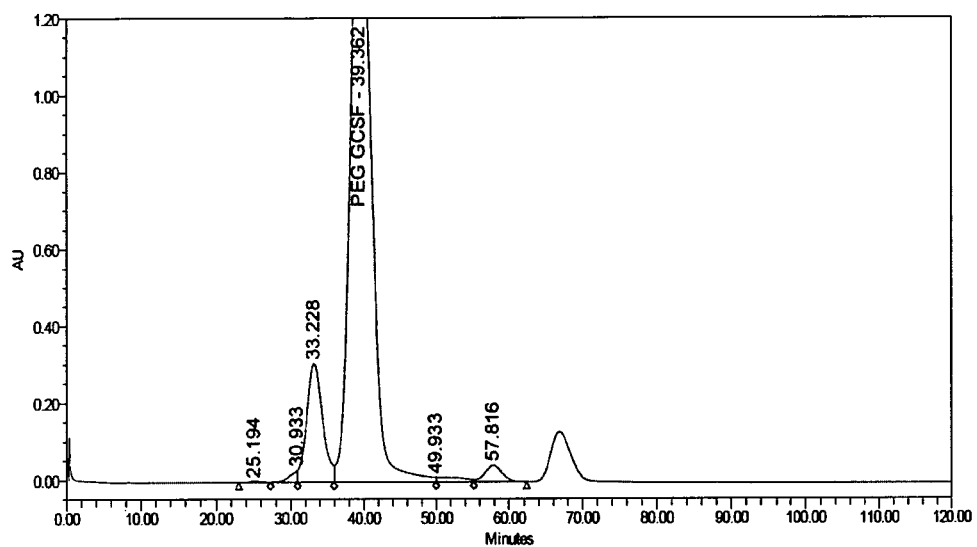

FIG. 12: SEC-HPLC profile of USV's crude pegylated r-metHuG-CSF wherein the pegylation is carried in presence of 5% sorbitol in acetate buffer, pH 5.0

DETAILED DESCRIPTION OF THE INVENTION

The covalent attachment of polyethylene glycl (PEG) to a therapeutic protein is frequently used to increase the half-life of that protein in patients while reducing their immunogenic response. Site-specific PEGylation is an attractive approach for maximizing the therapeutic value of PEGylated drugs because this process generates only PEGylated isomer with optimized properties. Amine-specific modification agents include PEG NHS ester, PEG tresylate, PEG aldehyde, PEG isothiocyanate, and several others. All react under mild conditions and are very specific for amino groups. The PEG-NHS ester is probably one of the more reactive agents; however, its high reactivity can make the PEGylation reaction difficult to control at large scale. PEG aldehyde forms an imine with the amino group, which is then reduced to a secondary amine with sodium cyanoborohydride. Sodium cyanoborohydride does not reduce disulfide bonds but the chemical is highly toxic and must be handled cautiously, particularly at lower pH where it becomes volatile. Due to multiple lysine residues on most proteins, site specific PEGylation can be a challenge. But as PEG aldehyde reagent reacts with unprotonated amino groups, it is possible to direct the PEGylation to lower-pK amino groups by performing the reaction at a lower pH. Generally the pK of the alpha-amino group is 1-2 pH units lower than the epsilon-amino group of lysine residues. By Pegylating the molecule at pH 7 or below, high selectivity for the N-terminus frequently can be attained. The approach is extremely useful for proteins wherein the N terminal portion is not essentially required for bioactivity.[1]

One specific aspect of the invention is an process for improving the pegylation reaction yield comprising conjugating r-metHuG-CSF to a PEG aldehyde at a free amine moiety at the N terminal end on the r-metHuG-CSF in a pegylation buffer solution comprising a polyol having the formula $C_nH_{2n+2}O_n$ where n is from 3 to 6, or a carbohydrate, or a derivative thereof. It was surprisingly found during buffer exchange of concentrated r-metHuG-CSF having a concentration of 2 mg/ml and above to pegylation buffer (acetate buffer, pH 5.0) where the protein tends to precipitate out causing 25% net loss of protein and hence results in decreased monopegylated product yield, but by just addition of a polyol having the formula of $C_nH_{2n+2}O_n$ where n is from 3 to 6, or a carbohydrate, or a derivative thereof to the pegylation buffer during buffer exchange resulted in increased pegylated product yield and prevented loss of r-metHuG-CSF. The pegylated product essentially had at least 80% monoPEGylated r-metHuG-CSF and pegylation efficiency of 98%. The N-terminal monopegylated r-metHuG-CSF had essentially a purity of >99% with total impurity not more than 1%.

Pegylation buffer as used herein means any aqueous buffer solutions made with any buffers known in the biochemical art that provide buffering from pH 4.0 to pH 6.0, with about pH 5 preferred for carrying out site-specific pegylation of r-metHuG-CSF. These buffers can include, but are not limited to acetate, citrate, glutamate, sorbate, succinate, 2-(N-Morpholino)-ethane sulfonic acid (MES), or phosphate. Useful buffer concentrations may range from 5 mM to 100 mM.

By polyols as used herein means any polyol selected from the group derived from the carbohydrates having at least three carbon atoms. These have the general formula $C_nH_{2n+2}O_n$, where n is from 3 to 6.

They include but are not limited to sorbitol, mannitol, erythritol, glycerol, xylitol and ribitol. In a particular embodiment of the invention the polyol is added to the pegylation buffer at an amount of 0.1% to 10% w/w, in particular at an amount of 0.5% to 5% w/w. Preferably the polyol of choice is also the one used for stabilizing the r-metHuG-CSF as well as PEG-r-metHuG-CSF formulation.

By carbohydrates as used herein means any of the carbohydrates having four or more carbon atoms preferably from 4 to 6 carbon atoms. In particular a mono-saccharide selected from the group consisting of glucose, fructose, mannose and galactose is preferred or a disaccharide selected from the group consisting of lactose, maltose trehalose and sucrose is preferred. In a particular embodiment of the invention the carbohydrate is added to the pegylation buffer at an amount of 0.1% to 10% w/w, in particular at an amount of 0.5% to 5% w/w.

By derivatives as used herein means derivatives including methyl glycosides, glucoronic acids, amino sugars, or N-acetyl glucosamines.

By storage buffer means any aqueous buffer solutions made with any buffers known in the biochemical art that provide buffering from pH 4.0 to pH 6.0, with about pH 5 preferred used as aqueous carrier vehicle for storing r-metHuG-CSF as well as PEG-r-metHuG-CSF. These buffers can include, but are not limited to acetate, citrate, glutamate, succinate, 2-(N-Morpholino)-ethane sulfonic acid (MES), or phosphate. Useful buffer concentrations may range from 0.5 mM to 100 mM.

By PEGylated product yield as used herein means the total PEGylated product formed including the monoPEGylated, and higher molecular weight dimers and aggregates as determined by SEC-HPLC.

By monoPEGylated product yield as used herein means the monoPEGylated product content as determined by SEC-HPLC.

By unreacted r-met-HuG-CSF as used herein means the r-met-HuG-CSF protein which has not reacted with PEG aldehyde.

By r-metHuG-CSF as used herein means recombinant, methionyl human granulocyte colony-stimulating factor (G-CSF), a 175 residue protein produced in *Escherichia coli*.

By PEG-r-met-HuG-CSF as used herein means PEGylating r-metHuG-CSF at the N terminal methionine with PEG aldehyde reagent using reductive alkylation in the presence of a reducing agent under conditions sufficient to drive the PEGylation at N terminal.

By pegylation reaction yield as used herein means the total amount of protein converted to the PEGylated conjugates including a mixture of monoPEGylated, higher MW dimers and aggregates as determined by size exclusion HPLC.

By gram scale as used herein means carrying out the pegylation of protein at least at one gram scale and above.

In different aspect, the present invention is an improved process to maximize the amount of mono-PEGylated product produced during the PEGylation reaction while minimizing the costs associated with manufacturing the mono-PEGylated product by eliminating the protein precipitation during concentration and subsequently during pegylation by just addition of a polyol having the formula of $C_nH_{2n+2}O_n$ where n is from 3 to 6, or a carbohydrate, or a derivative thereof prior to concentration and subsequently during buffer exchange to the pegylation buffer wherein the pegylated product yield is 98% and the mono-PEGylated species product yield is atleast 80% as against the pegylated product yield of 80% and the mono-PEGylated species product yield of 74.33% for the control.

Another aspect of the present invention is to minimize the impact on cost per gram of monoPEGylated r-metHuG-CSF. When optimizing a process for the manufacture of a protein drug, there are three main considerations: high product quality (purity, stability, and activity), process robustness, and low cost. Cost reduction is critical during upscaling the process at gram scale. The possible issues during an effective upscaling for a pegylation process involves large processing volumes at low protein concentrations. Hence concentration of protein prior to pegylation adds to the cost of production. Cost implications with use of ultrafiltration (UF) or diafiltration (DF) or tangential flow filtration (TFF) to concentrate the protein cannot be avoided. But further additional cost incurred by diafiltering the product to buffer exchange to the PEGylation buffer containing a reducing agent if eliminated can save substantial amount of pegylation cost. Also it is well known in the art that r-metHuG-CSF at higher concentration is quite unstable and has an iherent tendency to precipitate out. Hence a rapid PEGylation reaction is preferred to avoid instability of high concentration of protein which needs a stabilizer and reformation of S—S bonds involving the surface Cys.

Therefore, an essential aspect of the invention is total elimination of the second diafiltration step thereby avoiding buffer exchange to PEGylation buffer by just addition of mPEG-aldehyde to the storage buffer in presence of a reducing agent wherein surprisingly it was found that the monoPEGylated r-metHuG-CSF yield is still ≥80%. The invention envisages use of acetate buffer, pH 5.0 which is also storage buffer for Neupogen as well as Neulasta. The instant invention thus provides a simplified process of PEGylation by just addition of mPEG aldehyde reagent and sodium cyanoborohydride to the commercially available filgrastim formulation to achieve the desired effect.

Further to the above an essential aspect of the instant invention is to reduce the impact of the cost of the raw materials on production of monoPEG r-metHuG-CSF by optimizing the molar ratio of PEG aldehyde to r-metHuG-CSF. For amine specific modifications parameters to be considered when developing a PEGylation procedure include protein concentration, PEG-to-protein ratio (on a molar basis), temperature, pH and reaction time. Holtschlag et al., disclose a process for optimization of a PEGylation reaction using Design of Experiments by optimizing PEG/protein ratio, pH and reductant/protein ratio on the respective monoPEGylated product yield. The data demonstrated that the monoPEGylated species was highest at the following conditions: pH 6.74, a molar ratio of 3.0 for the reducing agent, and a PEG/protein ratio of 2.25 with an yield of 78.7%. However, when the cost and availability of the reagents were taken into account (in addition to the time required for pH adjustment in manufacturing) the conditions that resulted in both the highest mono-PEGylated species and the lowest cost were pH 7.0, a molar ratio of 2.0 for the reductant, and a PEG/protein ratio of 1.75 with an yield reduced to 72.1%. In the instant invention it was surprisingly found when the PEG/protein molar ratio when reduced from 5:1 to 2.5:1, the monoPEGylated product yield was still ≥80% wherein the reduction in cost per gram of the product was 1.5 fold.

Treuheit et al., described the formulation development for Neulasta (pegfilgrastim), and the analytical techniques used to monitor degradation during these studies. Stability was assessed as a function of pH, protein concentration, buffer type, tonicity modifiers and surfactant concentration under both accelerated conditions and quiescent long-term storage. Treuheit et al., disclosed the role of surfactants in formulations as to protect the protein at various potentially destabilizing interfaces and to alter the thermodynamic conformational stability of proteins. Alternately the use of surfactants stabilize protein by minimizing aggregation induced by freeze-thaw, quiescent storage, thermal stress and agitation. Polysorbate 20 was preferred over polysorbate 80 because it was available from a vegetable-derived source.

Kinstler et al. (2002), presented a site-directed method of joining proteins to polyethylene glycol for the preparation of essentially homogeneous PEG-protein derivatives with a single PEG chain conjugated to the amine terminus of the protein by conducting the reductive alkylation of proteins with PEG-aldehydes at lower pH. The working example illustrated the conditions as to a solution of r-metHuG-CSF (5 mg/ml) in 100 mM sodium acetate, pH 5.0, containing 20 mM sodium cyanoborohydride was added five fold molar excess of 6 kDa mPEG aldehyde and reactants were stirred in an ice bath. The extent of protein modification was monitored by size exclusion HPLC employing a Bio-Sil SEC250-5 column eluted with 100 mM sodium phosphate, 150 mM sodium chloride, 10 mM sodium azide, pH 6.8, at 1 ml/minute. At the end of 10 hours, 92% of the protein had been converted to the mono-PEG conjugate, the pH adjusted to 4.0 with 100 mM HCl and diluted 5-fold with 1 mM HCl. The mono-mPEG-r-metHuG-CSF conjugate was isolated by ion exchange chromatography using a HiLoad 16/10 SP Sepharose HP column equilibrated with 20 mM sodium acetate buffer, pH 4.0, and eluted with a linear 0-1 M NaCl gradient.

There is always a need to develop cost-effective processes for PEGylating proteins by optimizing the downstream processing and concentration steps by counteracting the in-process loss of PEGylated protein. Another element of the present invention is surprising finding wherein during isolating the monoPEG-r-metHuG-CSF using ion exchange chromatography and eluting said monoPEG-r-metHuG-CSF and further concentrating the pooled monoPEGylated r-metHuG-CSF against storage buffer having molarity in the range of 10 mM to 50 mM with 5% sorbitol or sucrose and essentially a non ionic surfactant yielded monoPEGylated r-metHuG-CSF with ≥99% as against the concentration step carried in the absence of the non ionic surfactant.

One embodiment of the present invention is a process for improving pegylation reaction yield of r-metHuG-CSF comprising conjugating r-metHuG-CSF to a PEG aldehyde at a free amine moiety at the N terminal end on the G-CSF in presence of a reducing agent in a pegylation buffer solution comprising a polyol having the formula $C_nH_{2n+2}O_n$ where n is from 3 to 6, or a carbohydrate, or a derivative thereof wherein the concentration of said polyol or carbohydrate or derivative thereof in the range of 0.1% to 10% w/w.

Second embodiment of the present invention is a process for gram scale production of PEG-r-metHuG-CSF comprising conjugating r-metHuG-CSF in storage buffer solution comprising a polyol having the formula $C_nH_{2n+2}O_n$ where n is from 3 to 6, or a carbohydrate, or a derivative thereof to a PEG aldehyde at a free amine moiety at the N terminal end on the r-metHuG-CSF in presence of a reducing agent the improvement being conjugating the r-metHuG-CSF in storage buffer solution having molarity in the range of 10 mM to 50 mM comprising a polyol having the formula $C_nH_{2n+2}O_n$ where n is from 3 to 6, or a carbohydrate, or a derivative thereof to a PEG aldehyde by elimination of step of buffer exchange to the pegylation buffer.

Third embodiment of the present invention is a process for gram scale production of PEG-r-metHuG-CSF comprising conjugating r-metHuG-CSF in storage buffer solution having molarity in the range of 10 mM to 50 mM comprising a polyol having the formula $C_nH_{2n+2}O_n$ where n is from 3 to 6, or a carbohydrate, or a derivative thereof to a PEG aldehyde at a free amine moiety at the N terminal end on the r-metHuG-CSF in presence of a reducing agent characterized in that the PEG aldehyde is added in stoichiometric molar ratio of 2.5 relative to r-metHuG-CSF.

Fourth embodiment of the invention is a process for gram scale production of PEG-r-metHuG-CSF comprising conjugating r-metHuG-CSF in storage buffer solution comprising a polyol having the formula $C_nH_{2n+2}O_n$ where n is from 3 to 6, or a carbohydrate, or a derivative thereof to a PEG aldehyde at a free amine moiety at the N terminal, isolating the monoPEG-r-metHuG-CSF using ion exchange chromatography and eluting and concentrating the pooled monoPEGylated r-metHuG-CSF against storage buffer having molarity in the range of 10 mM to 50 mM consisting essentially of polyol having the formula $C_nH_{2n+2}O_n$ where n is from 3 to 6 or carbohydrate or a derivative thereof and a non ionic surfactant characterized in that the purity of concentrated monoPEGylated r-metHuG-CSF is ≥99%.

EXAMPLES

Example-1

Concentration and Diafiltration (Buffer Exchange) of the r-metHuG-CSF:

The liquid stock solution of r-metHuG-CSF from USV (concentration ca 1.9 mg/ml supplied in 10 mM sodium acetate, 5% sorbitol pH 4.0) which was stored at 2-8° C., was aliquoted out from the stock. The protein was then concentrated to about 6-7 mg/ml. The sample was diluted twice the volume with 100 mM sodium phosphate buffer pH 5.0 containing 20 mM sodium cyanoborohydride and 5% Sorbitol. The dilution and concentration was done for 3 times with the buffer. The final diafiltered concentration was 6-7 mg/ml. The diafiltration procedure was done at 4° C. in an ice bath. The concentrated solution was then stored at 4° C. or taken for PEGylation reaction. The % recovery of the r-metHuG-CSF post buffer exchange and concentration was about 95% to 97%.

Example-2

Preparation of Pegylated r-metHuG-CSF:

The diafiltered, and the quantified protein obtained from Example 1 was taken in a 250 ml glass bottle. A buffer consisting of 100 mM sodium phosphate buffer pH 5.0 with 20 mM sodium cyanoborohydride and with/without 5% Sorbitol was added to the reaction mixture. The methoxy-polyethylene glycol-propionaldehyde (mPEG-aldehyde; SUN-BRIGHT ME-200AL from NOF Corp., Japan) of approximately 20 Kda was added to the above stirred solution of the protein. The mPEG-aldehyde was then transferred to the bottle containing protein solution. The protein concentration was maintained at 5 mg/ml. The reaction mixture was then stirred at 2-8° C., overnight. The reaction mixture was quenched by addition of 40 mM sodium acetate buffer pH 4.0 with and without 5% Sorbitol in the buffer (volume made to five times the reaction volume) (FIGS. 1 & 2).

The percentage conversion of r-metHuG-CSF was >98% wherein the pegylation was carried out in the presence of sorbitol.

Example-3

Purification Using Ion Exchange Chromatography:

The pegylated r-metHuG-CSF obtained from Example-2 was loaded to a weak cation exchange column of following specification:

System: AKTA UPC 100 medium pressure system

The pegylated protein was eluted in a gradient mode using the following buffer system.

Buffer A: 40 mM Sodium acetate in 5% Sorbitol pH 4.0

Buffer B: 40 mM Sodium acetate, 5% Sorbitol, 0.5M NaCl pH 4.0

The fractions containing the mono PEG-r-metHuG-CSF (>99%), were pooled.

Polysorbate 20 (Tween 20) was added to these fractions prior to concentration. The sample was concentrated and diafiltered with 10 mM sodium acetate, 5% Sorbitol, Tween 20. The final concentration achieved was >10 mg/ml, with purity of mono PEG r-metHuG-CSF >99% (FIG. 4). Table 1 illustrates the effect of addition of 5% sorbitol to the pegylation buffer and subsequent addition of tween-20 to the storage buffer prior to concentration.

TABLE 1

Comparative analysis for pegylation carried in the presence and absence of sorbitol

| | In the absence of sorbitol | | | | In the presence of 5% sorbitol | | | |
| --- | --- | --- | --- | --- | --- | --- | --- | --- |
| Step involved | % Aggregates | % Dimer | % mono pegylated r-metHuG-CSF | % unreacted r-metHuG-CSF | % Aggregates | % Dimer | % mono pegylated r-metHuG-CSF | % unreacted r-metHuG-CSF |
| Pegylation | 0.36 | 4.39 | 74.33 | 21.03 | 0.24 | 16.62 | 82.32 | 0.83 |
| Purification and pooling prior to concentration | NA | NA | NA | NA | 0.07 | 0.2 | 99.73 | — |
| Purification and concentration in the absence of tween 20 | 0.33 | 0.35 | 99.03 @ 0.953 mg/ml | 0.29 | 0.09 | 0.42 | 99.49 @ 5 mg/ml | — |
| | | | | | 0.17 | 0.73 | 99.11 @ 9.35 mg/ml | — |
| Purification and concentration in the presence of tween 20 | 0.20 | 0.18 | 99.26 @ 0.982 mg/ml | 0.36 | 0.09 | 0.14 | 99.76 @ 5 mg/ml | — |
| | | | | | 0.09 | 0.25 | 99.66 @ 10.52 mg/ml | — |

The USV's monopegylated r-metHuG-CSF was characterized using 1) Non-reducing SDS-PAGE of USV's purified pegylated r-metHuG-CSF (FIG. 3), 2) Size exclusion chromatography HPLC (SEC-HPLC) profile of USV's monopegylated r-metHuG-CSF overlayed with Neulasta (FIG. 6), 3) peptide mapping analysis (FIG. 5), 4) in vitro r-metHuG-CSF bioassay (FIG. 7), 5) in vivo testing in mice.

Example 4

Biological Activity:

NFS-60 cells (ATCC CRL 1838) grown in RPMI+10% FBS were used for PEG-r-metHuG-CSF cell proliferation assay. Cells were plated in 96 well plate and incubated with USV's monopegylated GCSF at concentration range 10-100 pg/ml for 72 hours in 37° C. and 5% $CO_2$ humidified incubator. 5 mg/ml MTT solution made in PBS was added in each well. Plates were incubated in 37° C. and 5% $CO_2$ humidified incubator for 4-5 hrs.

MTT is used for quantitative determination of cellular proliferation and activation in response to PEG-r-metHuG-CSF. The assay is based on cleavage of the yellow tetrazolium salt MTT, to purple formazan crystals by metabolic active cells. These crystals are then dissolved by adding acidified 25% SDS solution.

The solubilized formazan product was spectrophotometrically quantified using an ELISA reader at 570 nm. An increase in the number of living cells resulted in an increase in the total metabolic activity in the sample. This increase directly correlates to the amount of purple formazan crystals formed, as monitored by the absorbance.

Example 5

In-vivo Activity:

Pharmacokinetics and pharmacodynamics of pegylated r-metHuG-CSF was evaluated in male Sprague Dawley rats. A single subcutaneous dose (100 mcg/kg bodyweight) of pegylated r-metHuG-CSF (USV) was administered to the experimental animals. Blood samples were withdrawn at 0, 1, 2, 4, 6, 8, 12, 24, 48, 72, 96, 120, 144, 168, 192 and 216 hours post dosing. Blood samples were divided in two aliquots. Plasma was separated from one aliquot and concentration of r-metHuG-CSF was measured by ELISA using a commercially available kit. The second aliquot of blood was subjected to the estimation of absolute neutrophil count (ANC), a parameter for assessment of pharmacodynamic response. The monopegylated r-metHuG-CSF (USV) had an elimination half life of about 12 hours. The increase in ANC reached a peak at 48 hours and the ANC returned to pretreatment values at the end of 168 hours.

Example 6

Concentration and Diafiltration (Buffer Exchange) of the r-metHuG-CSF in Presence of 5% Sucrose:

The liquid stock solution of r-metHuG-CSF from USV (concentration ca 2.04 mg/ml) which was stored at 2-8° C., was aliquoted out from the stock. The protein was then concentrated to about 6-7 mg/ml. The sample was diluted twice the volume with 100 mM sodium phosphate buffer pH 5.0 containing 20 mM sodium cyanoborohydride and 5% Sucrose. The dilution and concentration was done for 3 times with the buffer. The final diafiltered concentration was 6-7 mg/ml. The concentrated solution was then stored at 4° C. or taken for PEGylation reaction. The % recovery of the r-metHuG-CSF post buffer exchange and concentration was about almost quantitative.

Example 7

Preparation of Pegylated r-metHuG-CSF in Presence of 5% Sucrose:

The diafiltered, and the quantified protein obtained from Example 1 was taken in a 250 ml glass bottle. A buffer consisting of 100 mM sodium phosphate buffer pH 5.0 with 20 mM sodium cyanoborohydride and with/without 5% Sucrose was added to the reaction mixture. The methoxy-polyethylene glycol-propionaldehyde (mPEG-aldehyde; SUNBRIGHT ME-200AL from NOF Corp., Japan) of approximately 20 Kda was added to the above stirred solution of the protein. The mPEG-aldehyde was then transferred to the bottle containing protein solution. The protein concentration was maintained at 5 mg/ml. The reaction mixture was then stirred at 2-8° C., overnight. The reaction mixture was quenched by addition of 40 mM sodium acetate buffer pH 4.0 with 5% Sucrose in the buffer (volume made to five times the reaction volume) (FIG. 8).

Example 8

Figure 10:
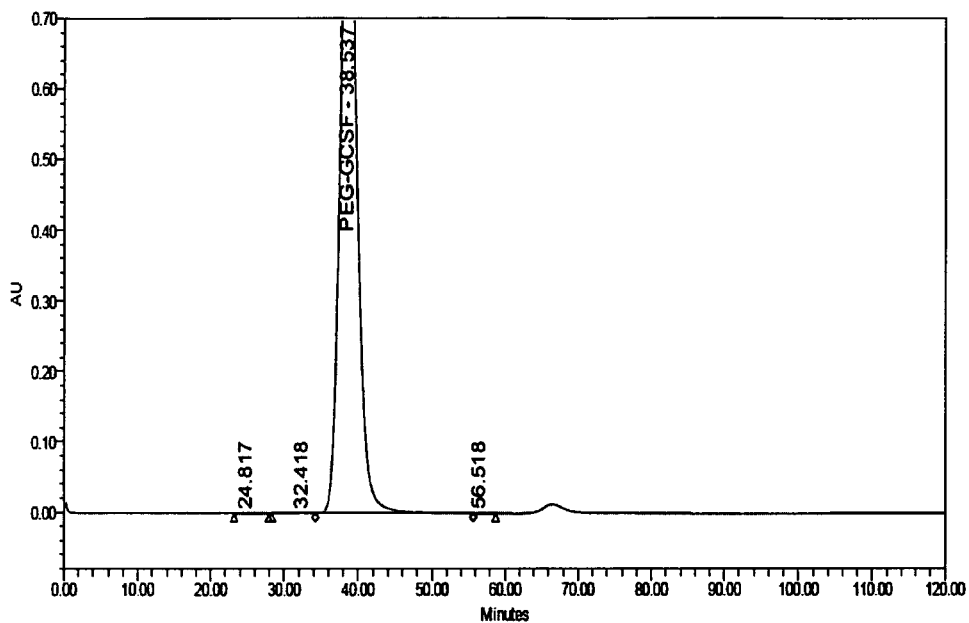

Preparation of Pegylation Process at 8 Gram Scale:
A) Concentration and Difiltration:

8 gm of Filgrastim API was concentrated to 1.6 liter using 5-kDA cassette. Concentrated protein solution was diafiltered against 100 mM sodium phosphate buffer pH 5.0+5% sorbitol. After difiltration protein solution was collected in 2-liter bottle. Protein content was estimated using UV 280 nm.
B) Pegylation:

Protein concentrated by TFF was adjusted to 5.5 mg/ml using above diafiltration buffer. Protein solution was then kept at 5° C. under stirring. Once the temperature of reaction mixture was below 7° C., 5.2 gm of methoxy-polyethylene glycol-propionaldehyde was added for every gram of protein. 111 ml of 200 mM Sodium cyanoborohydride stock solution was added per liter of protein solution to achieve 20 mM composition. Pegylation reaction was carried for 16 hrs at 5° C. under stirring. Mono PEG-r-metHuG-CSF after 16 hours of reaction was more than 80% (FIG. 9). Once completed, the reaction was stopped by diluting the reaction mixture with 4 times (v/v) with 50 mM sodium acetate pH 4.0+5% sorbitol at 10° C.
C) Ion Exchange Chromatography:

1.6 liter of CM-HP sepharose matrix packed in Quickscale 100 column was equilibrated with 50 mM sodium acetate pH 4.0+5% sorbitol at 10° C. Pegylated protein solution was diluted with water to achieve conductivity of less than 3 ms/cm before loading. After loading column was first washed with equilibration buffer and then protein was eluted using a linear gradient in the range of 0-500 mM of sodium chloride. Protein fractions of monomer purity greater than 99% were pooled together for next step.
D) Concentration and Difiltration:

10 ml of Tween 20 stock (3.3 mg/ml) solution was added per liter of pooled fraction. Pooled fractions were then concentrated by 10 kDa cassette to 2 mg/ml and then diafiltered against 10 mM Acetate (pH 4.0)+5% sorbitol+0.0033% Tween 20 buffer. After diafiltration, protein solution was concentrated to more than 10 mg/ml. Concentrated protein solution was then filtered by 0.2μ capsule filter to achieve protein concentration of more than 10 mg/ml and monomer purity greater than 99% (FIG. 10).

Example 9

Concentration and Diafiltration and Pegylation in Acetate Buffer (pH 4.0):

r-metHuG-CSF API was concentrated in 20 mM acetate buffer (pH 4.0) to 5.5 mg/ml. pH was then adjusted to 5.0 by using 2 M sodium acetate pH unadjusted. The pegylation reaction, ion exchange chromatography and concentration was performed as per procedure of Example 8 (FIG. 12).

Example 10

Concentration and Diafiltration and Pegylation in Acetate Buffer (pH 4.0) with protein:mPEG-aldehyde Ratio of 1:2.5:

2.6 gm of methoxy-polyethylene glycol-propionaldehyde was added per gram of protein instead of 5.2 gm and the reaction was carried out for 20 hours. The monoPEG r-metHuG-CSF yield was 80% in 20 mM acetate Buffer pH 5.0. The pegylation reaction, ion exchange chromatography and concentration was performed as per procedure of Example 8 (FIG. 11).

While the present invention is described above in connection with preferred or illustrative embodiments, these embodiments are not intended to be exhaustive or limiting of the invention. Rather, the invention is intended to cover all alternatives, modifications and equivalents included within its spirit and scope, as defined by the appended claims.

We claim:

1. A process for gram scale production of PEG-r-metHuG-CSF comprising conjugating r-metHuG-CSF in storage buffer solution having molarity in the range of 10 mM to 50 mM comprising a polyol having the formula $C_nH_{2n+2}O_n$ where n is from 3 to 6, or a carbohydrate, or a derivative selected from the group consisting of methyl glycosides, glucoronic acids, amino sugars and N-acetyl glucosamines thereof at pH 5.0 to a PEG aldehyde selectively at a free amine moiety at the N terminal end on the r-metHuG-CSF in presence of a reducing agent characterized in that the PEG aldehyde is added in stoichiometric molar ratio of 2.5 relative to r-metHuG-CSF, wherein the monopegylated product is having a purity of at least 80% and the other molecular size impurities are less than 10%.

2. The process of claim 1, wherein the storage buffer is selected from the group consisting of acetate, citrate, glutamate, sorbate, succinate, 2-(N-Morpholino)-ethane sulfonic acid (MES), or phosphate.

3. The process of claim 2, wherein the storage buffer is 20 mM acetate buffer, pH 5.0 with 5% sorbitol.

4. The process of claim 1 wherein the PEGylated product yield of monoPEGylated r-metHuG-CSF is at least 80%.

* * * * *